(12) United States Patent
Yuan et al.

(10) Patent No.: US 7,097,968 B2
(45) Date of Patent: Aug. 29, 2006

(54) METHODS AND COMPOSITIONS FOR ASSAYING HOMOCYSTEINE

(75) Inventors: Chong-Sheng Yuan, San Diego, CA (US); Abhijit Datta, Carlsbad, CA (US); Chao Dou, San Diego, CA (US)

(73) Assignee: General Atomics, San Diego, CA (US)

( * ) Notice: Subject to any disclaimer, the term of this patent is extended or adjusted under 35 U.S.C. 154(b) by 0 days.

(21) Appl. No.: 10/801,623

(22) Filed: Mar. 15, 2004

(65) Prior Publication Data

US 2005/0009128 A1 Jan. 13, 2005

Related U.S. Application Data

(60) Provisional application No. 60/486,865, filed on Jul. 10, 2003.

(51) Int. Cl.
*C12Q 1/00* (2006.01)
(52) U.S. Cl. .............................. 435/4; 435/15; 435/18
(58) Field of Classification Search .................... 435/4, 435/15, 18
See application file for complete search history.

(56) References Cited

U.S. PATENT DOCUMENTS

| | | | | |
|---|---|---|---|---|
| 4,981,801 | A * | 1/1991 | Suzuki et al. ............ | 435/286.1 |
| 5,631,127 | A | 5/1997 | Sundrehagen .................. | 435/4 |
| 5,827,645 | A | 10/1998 | Sundrehagen .................. | 435/4 |
| 5,854,023 | A | 12/1998 | Hillman et al. ............. | 435/69.1 |
| 5,861,294 | A | 1/1999 | Cowart et al. .............. | 435/194 |
| 5,885,767 | A | 3/1999 | Rozzell, Jr. .................... | 435/4 |
| 5,958,717 | A | 9/1999 | Sundrehagen ................ | 435/18 |
| 5,985,540 | A | 11/1999 | Tan et al. | |
| 6,063,581 | A | 5/2000 | Sundrehagen ............... | 435/7.1 |
| 6,376,210 | B1 | 4/2002 | Yuan .......................... | 435/18 |
| 6,436,658 | B1 | 8/2002 | Seman ....................... | 435/18 |
| 6,610,504 | B1 * | 8/2003 | Yuan .......................... | 435/15 |
| 6,664,073 | B1 | 12/2003 | Kawasaki et al. ............ | 435/25 |
| 6,686,172 | B1 | 2/2004 | Matsuyama et al. .......... | 435/18 |
| 2002/0119507 | A1 | 8/2002 | Kishimoto et al. ........... | 435/26 |
| 2002/0123088 | A1 | 9/2002 | Matsuyama et al. | |
| 2003/0138872 | A1 * | 7/2003 | Kawasaki et al. ............ | 435/25 |

FOREIGN PATENT DOCUMENTS

| | | |
|---|---|---|
| CN | 1560610 | 1/2005 |
| WO | WO-00/40973 | 7/2000 |
| WO | WO-00/77244 | 12/2000 |
| WO | WO-01/02600 | 1/2001 |
| WO | WO-03/040694 | 5/2003 |
| WO | WO 03/060478 | 7/2003 |

OTHER PUBLICATIONS

Nelson, DL et al. Lehninger Principles of Biochemistry, 3rd edition. Worth Publishers. 2000. pp. 640-642.*
Shapiro, SK. S-adenosylmethionine:L-homocysteine S-methyltransferase (*Saccharomyces cerevisiae*). Methods Enzymol. 1971. 17(Pt. B): 400-405.*
Chagoya de Sanchez, V et al. 24-hour changes of S-adenosylmethionine, S-adenosylhomocysteine adenosine and their metabolizing enzymes in rat liver: possible physiological significance in phospholipid methylation. Int. J. Biochem. 1991. 23(12):1439-1443.*
Kuchino, Y et al. Deficiency of S-adenosylmethionine-homocysteine methyltransferase activity in hepatoma cells. Cancer Research. 1977. 37: 206-208.*
Araki, et al., J. Chromatog., 422:43-52 (1987).
Ballal, et al., Cleveland Clinic Journal of Medicine, 64:543-549 (1997).
Boers, et al., J. Inher. Metab. Dis., 20:301-306 (1997).
Boushey, et al., JAMA, 274:1049-1057 (1995).
Cornell and Riscoe, Biochim. Biophys. Acta, 1396(1):8-14 (1998).
Coulter-Karis and Hershfield, Ann. Hum. Genet., 53(2):169-175 (1989).
Diaz-Arrastia, et al., Arch. Neurol., 55:1407-1408 (1998).
Ducloux, et al., Nephrol. Dial. Transplantl, 13:2890-2893 (1998).
Foody, et al., Clinician Reviews, 8:203-210 (1998).
Frantzen, et al., Clinical Chemsitry 44:2, 311-316 (1998).
Gore, Int. J. Biochem., 13(8):879-86 (1981).
Hornberger, et al., American J. of Public Health, 88:61-67 (1998).
Jacobsen, et al., Clin. Chem., 44:2238-2239 (1998).
Lai, et al., Mol. Cell. Biol., 17(5):2413-24 (1997).
Mansoor, et al., Anal. BioChem., 200:218-229 (1992).
Matsuyama, et al., Clinical Chemistry, 47:2155-2156 (2001).
McNalley et al., Biochem. Biophys. Res. Commun. 231:645-650 (1997).
Moghadasian, et al., Arch. Intern. Med., 157:2299-2307 (1997).
Perez-de la Mora et al., Anal. Biochem., 180(2):248-52 (1989).
Perry, "Homocystinuria" in Nyhan W.L. ed., Heritable disorders of amino acid metabolism. New York, John Wiley & Sons, pp. 395-428 (1974).
Refsum, et al., Annu. Rev. Medicine, 49:31-62 (1998).
Saksela and Raivio, Biochem. J., 315(1):235-9 (1996).
Scott, et al., "The etiology of neural tube defects" in Graham, I., Refsum, H., Rosenberg, I.H., and Ureland P.M. ed. "Homocysteine metabolism: from basic science to clinical medicine" Kluwer Academic Publishers, Boston, pp. 133-136 (1995).
Shapiro, Biochim. Biophys. Acta. 29:405-9 (1958).
Shapiro et al., J. Biol. Chem., 239(5):1551-6 (1964).

(Continued)

Primary Examiner—Francisco C. Prats
Assistant Examiner—Susan E. Fernandez
(74) Attorney, Agent, or Firm—Morrison & Foerster LLP

(57) ABSTRACT

This invention relates generally to the field of homocysteine detection. In particular, the invention provides a method for determining homocysteine presence or concentration in samples, which method comprises: contacting a sample containing or suspected of containing Hcy with a Hcy co-substrate and a Hcy converting enzyme in a Hcy conversion reaction to form a Hcy conversion product and a Hcy co-substrate conversion product; and assessing the Hcy co-substrate conversion product to determine the presence, absence and/or amount of the Hcy in the sample. A kit for assaying homocysteine based on the same principle is also provided.

20 Claims, 2 Drawing Sheets

OTHER PUBLICATIONS

Sigma-Aldrich catalog No. A5168.
Sigma-Aldrich catalog No. 01898.
Sigma-Aldrich catalog No. A9876.
Sigma-Aldrich catalog No. A1030.
Sigma-Aldrich catalog No. BCR647.
Sigma-Aldrich catalog No. 59023.
Sigma-Aldrich catalog No. 61311.
Sigma-Aldrich catalog No. 61306.
Sigma-Aldrich catalog No. K4388.
Sigma-Aldrich catalog No. P1903.
Sigma-Aldrich catalog No. P5788.
Sigma-Aldrich catalog No. 83330.
Singh et al., Eur. J. Biochem. 241:564-571 (1996).
Stabler, et al., J. Clin. Invest., 81:466-474 (1988).
Stehouwer, et al., Kidney International, 55:308-314 (1999).
Stein, et al., Arch. Intern. Med., 158:1301-1306 (1998).
Tan et al., Clinical Chemistry, 49:1029-1030 (2003).
Thanbichler et al., J. Bacteriol., 181(2):662-5 (1999).
Thomas et al., J Biol. Chem., 275(52):40718-24 (2000).
Ueland, et al., J. Lab. Clin. Med., 114:473-501 (1989).
Ueland, et al., Clin. Chem., 39:1764-1779 (1993).
International Search Report for PCT/US2004/022218, mailed on Jan. 7, 2005, 4 pages.
Complaint For Patent Infringement And Unfair Competition And Demand For Jury Trial, filed Oct. 9, 2001.
First Amended Complaint For Patent Infringement And Demand For Jury Trial, filed Dec. 19, 2001.
Answer To Amended Complaint And Counterclaim; Jury Demand, filed Jan. 8, 2002.
Plaintiff Axis-Shield ASA's Early Neutral Evaluation Conference Settlement Brief, filed Mar. 11, 2002.
Stipulation For Joint Dismissal Without Prejudice Of Complaint And Counter-Claim; [Proposed] Order, filed Mar. 22, 2002.
Complaint For Declaratory Relief, filed Oct. 11, 2005.
Answer And Counterclaim And Of Axis-Shield ASA, filed Oct. 27, 2005.
General Atomics' Reply To Counterclaim, filed Nov. 16, 2005.
Reply And Counterclaim Of Carolina Liquid Chemistries Corporation, filed Nov. 16, 2005.
Answer To Counterclaim Of Carolina Liquid Chemistries Corporation, filed Nov. 17, 2005.
Notice of Opposition to EP Patent 0 726 322, filed Jan. 16, 2004.
Patentee's Response to the Notices of Opposition, filed Oct. 1, 2004.
Response to Patentee's letter dated Oct. 1, 2004, filed Jul. 11, 2005.
Tanaka et al., Analytical Letters (1981) 14:111-118.
Selim and Greenberg, JBC (1958) 234:1474-1480.
Kashiwamata et al., Biochim. Biophys. Acta (1970) 212:488-500.
Binkley, JBC (1951) 101:531-534.
Shimizu et al., Biotechnol. Appl. Biochem. (1986) 8:153-159.
Porter et al., JBC (1991) 32:21616-21625.
Trewyn and Kerr, Journal of Biochemical and Biophysical Methods (1981) 4:299-307.
Loughlin et al., JBC (1964) 239:2888-2895.
Graham, Trends Cardiovasc. Med. (1991) 1:244-249.
Garras et al., Analytical Biochem. (1991) 199:112-118.
Frisell et al., JBC (1953) 207:709-716.
Sullivan and Hess, JBC (1936) 116:221-233.
EC4.2.1.22, www.chem.qmul.ac.uk/iubmb/enzyme/EC4/2/1/22.html.
Yamaguchi and Hosokawa, Methods in Enzymology (1987) 143:395-403.
Kotb and Kredich, J. Biol. Chem. (1985) 260(7):3923-30.
Tanaka et al., J. Applied Biochem. (1980) 2:439-444.
Bruton and Cox, Eur. J. Biochem. (1979) 100:301-308.
Homogeneous Enzymic Homocysteine Reagent package insert from Carolina Liquid Chemistries.

* cited by examiner

Figure 1. Co-Substrate Conversion Product Based Enzyme Cycling Assay of Homocysteine

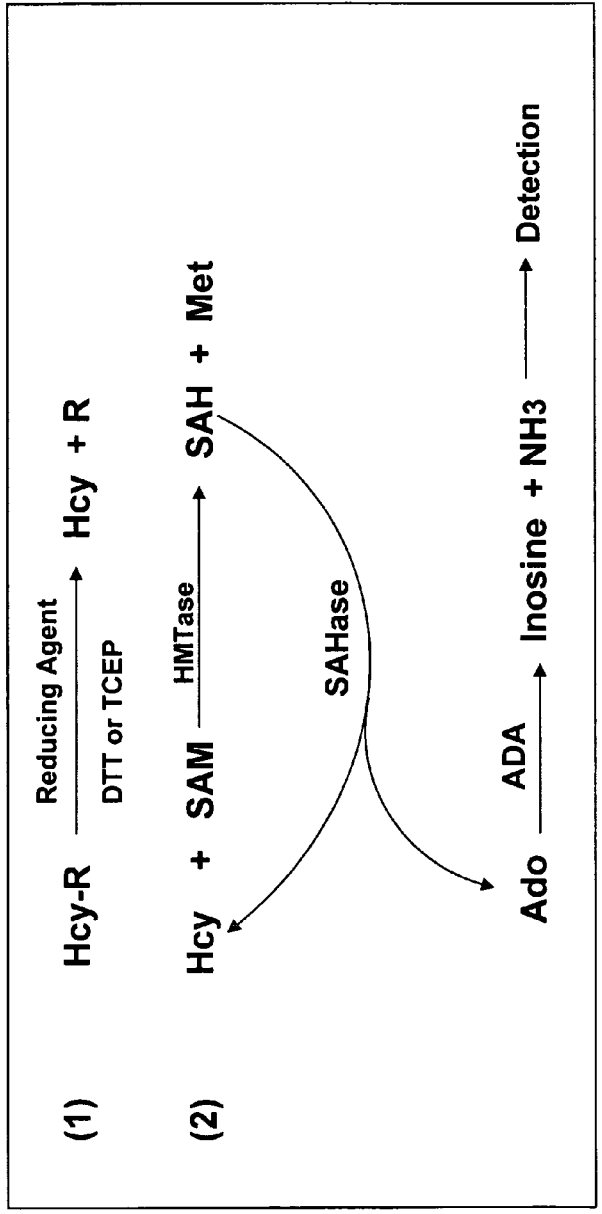

Hcy-R : oxidized homocysteine, R: protein, Hcy, Cys or other thio compounds; Hcy: reduced homocysteine (*substrate*)

SAM: S-adenosyl-L-methionine (*co-substrate*); HMTase: Homocysteine-methionine methyltransferase SAH: S-adenosyl-L-homocysteine (*co-substrate conversion product*);

SAHase: S-adenosyl-L-homocysteine hydrolase; ADA: Adenosine deaminase

METHODS AND COMPOSITIONS FOR ASSAYING HOMOCYSTEINE

CROSS-REFERENCE TO RELATED APPLICATIONS

This application claims the priority benefit of provisional application U.S. Ser. No. 60/486,865, filed Jul. 10, 2003, the contents of which are incorporated by reference in their entirety.

TECHNICAL FIELD

This invention relates generally to the field of homocysteine detection. In particular, the invention provides a method for determining homocysteine (Hcy) presence or concentration in samples in which homocysteine reacts with a Hcy co-substrate in a Hcy conversion reaction catalyzed by a Hcy converting enzyme to form a Hcy conversion product and a Hcy co-substrate conversion product, and the Hcy co-substrate conversion product is assessed to determine the presence and/or concentration of the Hcy in the sample. A kit for assaying homocysteine based on the same principle is also provided.

BACKGROUND OF THE INVENTION

Total concentration of homocysteine in body fluids, such as plasma or serum, is an important marker for disease. For example, homocysteine quantification can be an important risk indicator for cardiovascular disease, can be a sensitive marker of cobalamin and folate deficiencies, and can be used to diagnose in-born errors in metabolism known as homocystinuria. Homocysteine quantification has also been reported as useful in assessing birth defects in pregnant women and cognitive impairment in the elderly. See Frantzen, et al., Enzyme Conversion Immunoassay for Determining Total Homocysteine in Plasma or Serum, Clinical Chemistry 44:2, 311–316 (1998).

Homocysteine (Hcy) is a thiol-containing amino acid formed from methionine during S-adenosylmethionine-dependent transmethylation reactions. Intracellular Hcy is remethylated to methionine, or is irreversibly catabolized in a series of reactions to form cysteine. Intracellular Hcy is exported into extracellular fluids such as blood and urine, and circulates mostly in oxidized form, and mainly bound to plasma protein (Refsum, et al., *Annu. Rev. Medicine*, 49:31–62 (1998)). The amount of Hcy in plasma and urine reflects the balance between Hcy production and utilization. This balance may be perturbed by clinical states characterized by genetic disorders of enzymes involved in Hcy transsulfuration and remethylation (e.g., cystathionine β-synthase and $N^{5,10}$-methylenetetrahydrofolate reductase or dietary deficiency of vitamins (e.g., vitamin $B_6$, $B_{12}$ and folate) involved in Hcy metabolism (Baual, et al., *Cleveland Clinic Journal of Medicine*, 64:543–549 (1997)). In addition, plasma Hcy levels may also be perturbed by some medications such as anti-folate drugs (e.g., methotrexate) used for treatments of cancer or arthritis (Foody, et al., *Clinician Reviews*, 8:203–210 (1998))

Severe cases of homocysteinemia are caused by homozygous defects in genes encoding for enzymes involved in Hcy metabolisms. In such cases, a defect in an enzyme involved in either Hcy remethylation or transsulfuration leads to as much as 50-fold elevations of Hcy in the blood and urine. The classic form of such a disorder, congenital homocysteinemia (Hcyemia), is caused by homozygous defects in the gene encoding cystathionine β-synthase (CBS). These individuals suffer from thromboembolic complications at an early age, which result in stroke, myocardial infarction, renovascular hypertension, intermittent claudication, mesenteric ischemic, and pulmonary embolism. Such patients may also exhibit mental retardation and other abnormalities resembling ectopia lentis and skeletal deformities (Perry T., *Homocysteine: Selected aspects in Nyham W. L. ed. Heritable disorders of amino acid metabolism*. New York, John Wiley & Sons, pp. 419–451 (1974)). It is also known that elevated Hcy levels in pregnant women is related to birth defects of children with neurotube closures (Scott, et al., "The etiology of neural tube defects" in Graham, L, Refsum, H., Rosenberg, I. H., and Ureland P. M. ed. "*Homocysteine metabolism: from basic science to clinical medicine*" Kluwer Academic Publishers, Boston, pp. 133–136 (1995)). Thus, the diagnostic utility of Hcy determinations has been well documented in these clinical conditions.

It has been demonstrated that even mild or moderately elevated levels of Hcy also increase the risk of atherosclerosis of the coronary, cerebral and peripheral arteries and cardiovascular disease (Boushey, et al., *JAMA*, 274:1049–1057 (1995)). The prevalence of Hcyemia was shown to be 42%, 28%, and 30% among patients with cerebral vascular disease, peripheral vascular disease and cardiovascular disease, respectively (Moghadasian, et al., *Arch. Intern. Med.*, 157:2299–2307 (1997)). A meta-analysis of 27 clinical studies calculated that each increase of 5 µM in Hcy level increases the risk for coronary artery disease by 60% in men and by 80% in women, which is equivalent to an increase of 20 $mg/dl^{-1}$ (0.5 $mmol/dl^{-1}$) in plasma cholesterol, suggesting that Hcy, as a risk factor, is as strong as cholesterol in the general population. Results from these clinical studies concluded that hyperhomocysteinemia is an emerging new independent risk factor for cardiovascular disease, and may be accountable for half of all cardiovascular patients who do not have any of the established cardiovascular risk factors (e.g., hypertension, hypercholesterolemia, cigarette smoking, diabetes mellitus, marked obesity and physical inactivity).

Mild homocysteinemia is mainly caused by heterozygosity of enzyme defects. A common polymorphism in the gene for methylenetetrahydrofolate reductase appears to influence the sensitivity of homocysteine levels to folic acid deficiency (Boers, et al., *J. Inher. Metab. Dis.*, 20:301–306 (1997)). Moreover, plasma homocysteine levels are also significantly increased in heart and renal transplant patients (Ueland, et al., *J. Lab. Clin. Med.*, 114:473–501 (1989)), Alzheimer patients (Jacobsen, et al., *Clin. Chem.*, 44:2238–2239 (1998)), as well as in patients of non-insulin-dependent diabetes mellitus (Ducloux, et al., *Nephrol. Dial. Transplantl*, 13:2890–2893 (1998)). The accumulating evidence linking elevated homocysteine with cardiovascular disease has prompted the initiation of double-blind, randomized and placebo controlled multicenter clinical trials to demonstrate the efficacy of lowering plasma Hcy in preventing or halting the progress of vascular disease (Diaz-Arrastia, et al., *Arch. Neurol.*, 55:1407–1408 (1998)). Determination of plasma homocysteine levels should be a common clinical practice.

As a risk factor for cardiovascular disease, the determination of total plasma Hcy levels (reduced, oxidized and protein-bound) has been recommended in clinical setting (Homberger, et al., *American J. of Public Health*, 88:61–67 (1998)). Since 1982, several methods for determining total plasma Hcy have been described (Mansoor, et al., *Anal.*

BioChem., 200:218–229 (1992); Steir, et al., *Arch. Intern. Med.*, 158:1301–1306 (1998); Ueland, et al., *Clin. Chem.*, 39:1764–1779 01993); and Ueland, et al., *"Plasma homocysteine and cardiovascular disease"* in Francis, R. B. Jr. eds. *Atherosclerotic Cardiovascular Disease, Hemostasis, and Endothelial Function*. New York, Marcel Dokker, pp. 183–236 (1992); see, also, Ueland, et al., *"Plasma homocysteine and cardiovascular disease"* in Francis, R. B. Jr. eds. *Atherosclerotic Cardiovascular Disease, Hemostasis, and Endothelial Function*. New York, Marcel Dokker, pp. 183–236 (1992)). The assay of total Hcy in plasma or serum is complicated by the fact that 70% of plasma Hcy is protein-bound and 20–30% exists as free symmetric or mostly asymmetric mixed disulfides. Free reduced Hcy exists in only trace amounts (Stehouwer, et al., *Kidney International*, 55308–314 (1999)).

Most of the methods require sophisticated chromatographic techniques such as HPLC, capillary gas chromatography, or mass spectrometry (GC/MS) to directly or indirectly (e.g., enzymatic conversion of Hcy to SAH (S-adenosylhomocysteine) by SAH hydrolase followed by HPLC or TLC separation) measure Hcy. Radioenzymatic conversion of Hcy to radiolabeled SAH by SAH hydrolase prior to TLC separation has also been used. In these assays, chromatographic separation, which is often time-consuming and cumbersome to perform, is a common key step of these methods. More particularly, these methods require highly specialized and sophisticated equipment and well-trained analytic specialists. The use of such equipment is generally not well-accepted in routine clinical laboratory practice.

Immunoassays for Hcy that use a monoclonal antibody against SAH (Araki, et al., *J. Chromatog.*, 422:43–52 (1987)) are also known. These assays are based upon conversion of Hcy to SAH, which is then detected by a monoclonal antibody. Monoclonal antibody against albumin-bound Hcy has been developed for determination of albumin-bound Hcy (Stabler, et al., *J. Clin. Invest.*, 81:466–474 (1988)), which is the major fraction of total plasma Hcy. Other immunological protocols are also available (see, e.g., U.S. Pat. Nos. 5,631,127, 5,827,645, 5,958,717, 6,063,581 and 5,885,767). Though immunoassays avoid a time-consuming chromatographic separation step and are amenable to automation, production of monoclonal antibody is expensive, somewhat unpredictable, and often requires secondary or even tertiary antibodies for detection. Recently, enzymatic methods for homocysteine assay have been reported (Matsuyama, et al., *Clinical Chemistry*, 47:2155–2156 (2001); Tan et al., *Clinical Chemistry*, 49:1029–1030 (2003); U.S. Pat. Nos. 5,885,767, 5,998,191, 6,046,017, 6,174,696, 6,436,658 and 6,664,073 B1), all of these describe homocysteine assays based on the assessment of homocysteine conversion products generated by homocysteine converting enzymes.

Other methods for determining homocyteine in a sample are described in U.S. Pat. No. 6,686,172 and U.S. patent application Pub. No. 2002/0119507.

An efficient and accurate assay, that can be carried o highly skilled personnel or complex analytical chemistry equipment, has been needed. The present invention addresses the above and other related concerns in the art.

BRIEF SUMMARY OF THE INVENTION

In one aspect, the present invention is directed to an assay for homocysteine in a sample. According to this assay, a sample containing or suspected of containing homocysteine (Hcy) is contacted with a Hcy co-substrate and a Hcy converting enzyme in a Hcy conversion reaction to form a Hcy conversion product and a Hcy co-substrate conversion product; and the Hcy co-substrate conversion product is assessed to determine the presence, absence and/or amount of the Hcy in said sample.

In some embodiments of the invention, the Hcy co-substrate conversion product is assessed without chromatographic separation.

In some embodiments, the Hcy co-substrate is S-adenosylmethionine (SAM), the Hcy converting enzyme is S-adenosylmethionine (SAM)- dependent homocysteine S-methyltransferase, the Hcy conversion product is methionine (Met) and the Hcy co-substrate conversion product is S-adenosyl-L-homocysteine (SAH), and the SAH is assessed to determine the presence, absence and/or amount of the Hcy in the sample.

The SAM can be used in any suitable form. For example, the SAM is added to the sample directly. In another example, the SAM is produced by a further reaction, e.g., produced from ATP and Met by a SAM synthase.

The SAH may be converted to Hcy and adenosine (Ado), and Ado is assessed to determine the presence, absence and/or amount of the Hcy in the sample. In some embodiments, the SAH is contacted with a SAH hydrolase to generate Hcy from SAM, which is cycled into the Hcy conversion reaction by the SAM-dependent homocysteine S-methyltransferase to form a Hcy co-substrate based enzyme cycling reaction system, and adenosine (Ado), which is assessed to determine the presence, absence and/or amount of the Hcy in the sample.

The Ado may be assessed by any suitable methods known in the art such as immunological or enzymatic methods. The Ado may be assessed directly or indirectly. For example, the Ado may be assessed indirectly by assessing a co-substrate or a reaction product of adenosine conversion by an adenosine converting enzyme. In some embodiments, the adenosine converting enzyme is an adenosine kinase and the reaction product is Adenosine 5'-monophosphate. In other embodiments, the adenosine converting enzyme is an adenosine deaminase and the reaction products are ammonium and inosine.

In one aspect, the present invention is directed to a method for assaying homocysteine (Hcy) in a sample, which method comprises: a) contacting a sample containing or suspected of containing Hcy with a Hcy co-substrate and a Hcy converting enzyme in a Hcy conversion reaction to form a Hcy conversion product and a Hcy co-substrate conversion product, wherein the Hcy co-substrate is S-adenosylmethionine (SAM), the Hcy converting enzyme is S-adenosylmethionine (SAM)- dependent homocysteine S-methyltransferase, the Hcy conversion product is methionine (Met) and the Hcy co-substrate conversion product is S-adenosyl-L-homocysteine (SAH), and b) assessing the SAH to determine the presence, absence and/or amount of the Hcy in the sample, wherein the SAH is assessed without chromatographic separation.

The SAM can be used in any suitable form. For example, the SAM is added to the sample directly. In another example, the SAM is produced by a further reaction, e.g., produced from ATP and Met by a SAM synthase.

The SAH may be assessed by any suitable methods known in the art such as immunological or enzymatic methods. For example, SAH may be assessed by assessing binding between SAH and mutant SAH binding enzyme, e.g., a mutant SAH hydrolase that has binding affinity for Hcy, SAH or adenosine but has attenuated catalytic activity.

In one example, the assessment of SAH does not involve an enzymatic reaction generating $H_2O_2$ and detection of $H_2O_2$.

In another example, the SAH may be assessed by using an antibody which specifically binds to the SAH. The antibody may be monoclonal or polyclonal. The antibody may also be bound to a carrier matrix. Any suitable immunoassay formats, e.g., sandwich and competition assay formats, can be used.

The methods of the invention may be used for assaying homocysteine in any sample, including, but not limited to, a body fluid or a biological tissue. The body fluid may be selected from the group consisting of urine, blood, plasma, serum, saliva, semen, stool, sputum, cerebral spinal fluid, tears, mucus and amniotic fluid. In some embodiments, the body fluid is blood. In some embodiments, the blood sample is further separated into a plasma or serum fraction.

In some embodiments, prior to or concurrently with the contact between the sample and the Hcy co-substrate and the Hcy converting enzyme, oxidized or conjugated Hcy in the sample is converted into reduced Hcy. In some embodiments, the sample is subjected to treatment by dithiothreitol, tris(2-carboxyethyl)-phosphine hydrochloride (TCEP) or other reducing agent, in appropriate amounts to produce free homocysteine in the sample.

The method of the invention may further comprise a step of removing the reducing agent used to convert oxidized or conjugated Hcy into reduced Hcy prior to or concurrently with contacting the sample with the Hcy co-substrate and the Hcy converting enzyme. For example, the reducing agent can be removed by addition of N-ethylmaleimide or other thio-reacting compounds.

Still another aspect of the present invention is directed to a kit for determining presence or concentration of homocysteine in a sample, which kit comprises: a) a Hcy converting enzyme; b) a Hcy co-substrate; and c) a reagent for assessing Hcy co-substrate conversion product.

In some embodiments, the Hcy co-substrate is S-adenosylmethionine (SAM), the Hcy converting enzyme is a S-adenosylmethionine (SAM)- dependent homocysteine S-methyltransferase, the Hcy co-substrate conversion product is S-adenosyl-L-homocysteine (SAH), and the reagent for assessing Hcy co-substrate conversion product is a reagent for assessing SAH. In some embodiments, the kit further comprises a reagent, e.g., a SAH hydrolase, to generate Hcy from SAM, which is cycled into the Hcy conversion reaction by the SAM-dependent homocysteine S-methyltransferase to form a Hcy co-substrate based enzyme cycling reaction system, and adenosine (Ado).

The invention also provides a kit for assaying Hcy in a sample, which kit comprises: a) a S-adenosylmethionine (SAM)- dependent homocysteine S-methyltransferase; b) S-adenosylmethionine (SAM) or ATP, Met and a SAM synthase; c) a SAH hydrolase; and d) a reagent for assessing adenosine (Ado). The reagent for assessing Ado may be an adenosine converting enzyme other than the SAH hydrolase, such as an adenosine kinase and an adenosine deaminase.

The invention also provides a kit for assaying Hcy in a sample, which kit comprises: a) a S-adenosylmethionine (SAM)- dependent homocysteine S-methyltransferase; b) S-adenosylmethionine (SAM) or ATP, Met and a SAM synthase; and c) a reagent for assessing SAH, wherein the kit does not comprise an enzyme or a reagent for generating $H_2O_2$ and a reagent for detecting $H_2O_2$.

In some embodiments, the kit of the invention further comprises a reducing agent such as dithiothreitol (DTT) or TCEP.

The kit of the invention may be in any suitable packaging and may also include instructions for practicing methods described herein. The kit may optionally include additional components such as buffers.

The assays described herein can be used for any suitable purposes, e.g., prognostic, diagnostic, drug screening or treatment monitoring purposes. The assays readily can be automated. In addition, the assays can be adapted for use in point of care systems and in home test kits. For example, blood test point of care systems can be adapted for measuring homocysteine levels using methods provided herein. Home test kits may also be adapted for use with the methods provided herein.

BRIEF DESCRIPTION OF THE DRAWINGS

FIG. 1 illustrates an exemplary assay method for homocysteine. Hcy: L-homocysteine; SAM: S-adenosylmethionine; HMTase: SAM-dependent homocysteine S-methyltransferase; and SAHase: S-adenosyl-L-homocysteine hydrolase.

DETAILED DESCRIPTION OF THE INVENTION

Figure 2:
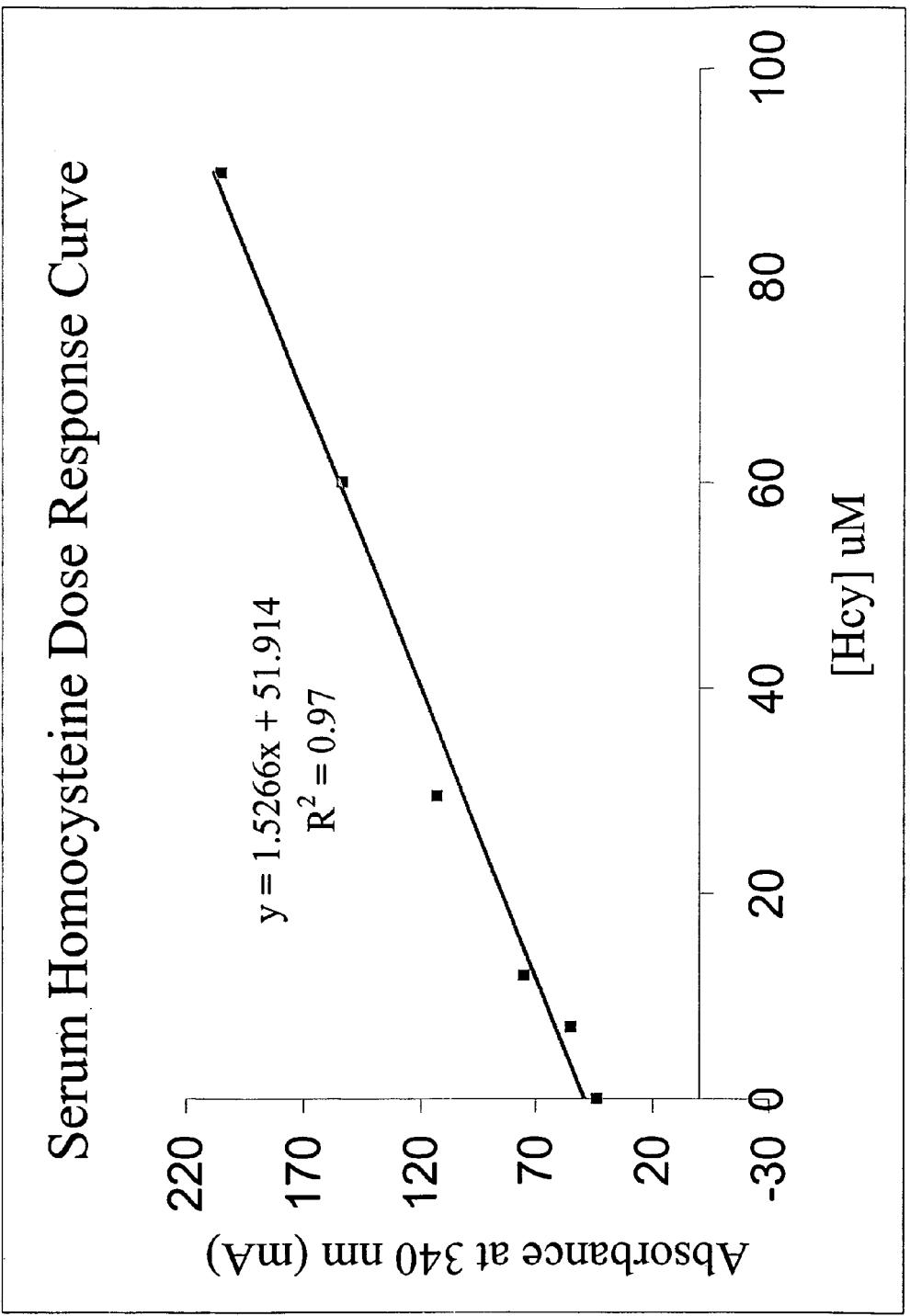
FIG. 2 depicts a serum homocysteine dose response curve obtained in the experiment described in Example 1.

For clarity of disclosure, and not by way of limitation, the detailed description of the invention is divided into the subsections that follow.

A. DEFINITIONS

Unless defined otherwise, all technical and scientific terms used herein have the same meaning as is commonly understood by one of ordinary skill in the art to which this invention belongs. All patents, applications, published applications and other publications referred to herein are incorporated by reference in their entirety. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, "a" or "an" means "at least one" or "one or more."

As used herein, "homocysteine (Hcy)" refers to a compound with the following molecular formula: $HSCH_2CH_2CH(NH_2)COOH$. Biologically, Hcy is produced by demethylation of methionine and is an intermediate in the biosynthesis of cysteine from methionine. The term "Hcy" encompasses free Hcy (in the reduced form) and conjugated Hcy (in the oxidized form). Hcy can conjugate with proteins, peptides, itself or other thiols through disulfide bond.

As used herein, "homocysteine (Hcy) conversion reaction" refers to a reaction in which a compound reacts with a Hcy molecule during which a chemical group (e.g., a methyl group) is transferred from the compound to the Hcy molecule to form reaction products. The compound that reacts with the Hcy molecule and provides the chemical group is referred to as "homocysteine (Hcy) co-substrate." The enzyme that catalyzes the reaction is referred to as "homocysteine (Hcy) converting enzyme." The reaction product that contains the whole or part of the original Hcy molecule is referred to as "homocysteine (Hcy) conversion product." The reaction product that does not contain any element from the original Hcy molecule is referred to as "Hcy co-substrate conversion product."

As used herein, "SAM-dependent homocysteine S-methyltransferase" refers to an enzyme that catalyzes formation of methionine and S-adenosyl-L-homocysteine (SAH) from homocysteine and S-adenosylmethionine (SAM). It is intended to encompass SAM-dependent homocysteine S-methyltransferase with conservative amino acid substitutions that do not substantially alter its activity.

As used herein, "SAH hydrolase" refers to an ubiquitous eukaryotic enzyme, which is also found in some prokaryotes, which catalyzes hydrolysis of SAH to adenosine (Ado) and Hcy. SAH hydrolase also catalyzes the formation of SAH from Ado and Hcy. The co-enzyme of SAH hydrolase is $NAD^+$/NADH. SAH hydrolase may have several catalytic activities. In the hydrolytic direction, the first step involves oxidation of the 3'-hydroxyl group of SAH (3'-oxidative activity) by enzyme-bound $NAD^+$ ($E-NAD^+$), followed by µ-elimination of L-Hcy to give 3'-keto-4', 5'-didehydro-5'-deoxy-Ado. Michael addition of water to the 5'-position to this tightly bound intermediate (5'-hydrolytic activity) affords 3'-keto-Ado, which is then reduced by enzyme-bound NADH (E-NADH) to Ado (3'-reduction activity). It is intended to encompass SAH hydrolase with conservative amino acid substitutions that do not substantially alter its activity.

As used herein the term "assessing" is intended to include quantitative and qualitative determination in the sense of obtaining an absolute value for the amount or concentration of the analyte, e.g., homocysteine or Ado, present in the sample, and also of obtaining an index, ratio, percentage, visual or other value indicative of the level of analyte in the sample. Assessment may be direct or indirect and the chemical species actually detected need not of course be the analyte itself but may for example be a derivative thereof or some further substance.

As used herein, "adenosine deaminase" refers to an enzyme that catalyzes the deamination of adenosine to form inosine. It is intended to encompass adenosine deaminase with conservative amino acid substitutions that do not substantially alter its activity.

As used herein, "adenosine kinase" refers to an enzyme that catalyzes the formation of adenosine 5'-monophosphate and ADP from adenosine and ATP. It is intended to encompass adenosine kinase with conservative amino acid substitutions that do not substantially alter its activity.

As used herein, "serum" refers to the fluid portion of the blood obtained after removal of the fibrin clot and blood cells, distinguished from the plasma in circulating blood.

As used herein, "plasma" refers to the fluid, noncellular portion of the blood, distinguished from the serum obtained after coagulation.

As used herein, "production by recombinant means" refers to production methods that use recombinant nucleic acid methods that rely on well known methods of molecular biology for expressing proteins encoded by cloned nucleic acids.

As used herein, "fluid" refers to any composition that can flow. Fluids thus encompass compositions that are in the form of semi-solids, pastes, solutions, aqueous mixtures, gels, lotions, creams and other such compositions.

As used herein, "sample" refers to anything which may contain an analyte for which an analyte assay is desired. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

As used herein, "disease or disorder" refers to a pathological condition in an organism resulting from, e.g., infection or genetic defect, and characterized by identifiable symptoms.

As used herein, "antibody" includes not only intact polyclonal or monoclonal antibodies, but also fragments thereof (such as Fab, Fab', $F(ab')_2$, Fv), single chain (ScFv), a diabody, a multi-specific antibody formed from antibody fragments, mutants thereof, fusion proteins comprising an antibody portion, and any other modified configuration of the immunoglobulin molecule that comprises an antigen recognition site of the required specificity. An antibody includes an antibody of any class, such as IgG, IgA, or IgM (or sub-class thereof), and the antibody need not be of any particular class.

B. METHODS FOR ASSAYING HOMOCYSTEINE

The invention provides a method for assaying homocysteine (Hcy) in a sample, which method comprises: a) contacting a sample containing or suspected of containing Hcy with a Hcy co-substrate and a Hcy converting enzyme in a Hcy conversion reaction to form a Hcy conversion product and a Hcy co-substrate conversion product; and b) assessing said Hcy co-substrate conversion product to determine the presence, absence and/or amount of said Hcy in said sample.

In some embodiments, the Hcy co-substrate conversion product is assessed without chromatographic separation.

In some embodiments, the Hcy converting enzyme is a S-adenosylmethionine (SAM)- dependent homocysteine S-methyltransferase. When a SAM- dependent homocysteine S-methyltransferase is used as the Hcy converting enzyme, the Hcy co-substrate is S-adenosylmethionine (SAM), the Hcy conversion product is methionine (Met) and the Hcy co-substrate conversion product is S-adenosyl-L-homocysteine (SAH), and the SAH is assessed to determine the presence, absence and/or amount of the Hcy in the sample.

Any S-adenosylmethionine (SAM)-dependent homocysteine S-methyltransferase that transfers a methyl group from SAM to Hcy can be used. For example, S-adenosylmethionine:L-homocysteine S-methyltransferase described by Shapiro and Stanley K (Methods Enzymol. 17 Pt.B, Sulfur Amino acids, pp. 400–405 (1971)) and Shapiro SK (*Biochim. Biophys. Acta.* 29:405–9 (1958)) can be used. The homocysteine S-methyltransferase (EC 2.1.1.10) encoded by the nucleic acid having the following GenBank Accession No. AF297394 and the amino acid sequence having the following GenBank Accession Nos. AAG10301, CAA16035, NP_856132, NP_302039, CAD97346, T51939, T51941 and CAC30428 can also be used. Preferably, the SAM-dependent homocysteine S-methyltransferase from *Escherichia coli.* (Thanbichler et al., *J. Bacteriol,* 181(2):662–5 (1999)) or *S. cerevisiae* (Shapiro et al., *J. Biol. Chem.,* 239(5):1551–6 (1964) and Thomas et al., *J. Biol. Chem.,* 275(52):40718–24 (2000)) can be used.

The SAM can be used in any suitable form. For example, the SAM is added to the sample directly. In another example, the SAM is produced by a further reaction, e.g., produced from ATP and Met by a SAM synthase.

SAH may be assessed using any methods known in the art. For example, SAH may be assessed by using an antibody which specifically binds to SAH. Antibodies may be polyclonal or monoclonal. Examples of antibodies specific to SAH are described in U.S. Pat. Nos. 5,631,127 and 6,063,581. Antibodies specific for SAH can also be generated using methods known in the art, for example methods described in U.S. Pat. Nos. 5,631,127 and 6,063,581.

Any immunological assays may be used for detecting SAH with the antibody specific to SAH, for example, competition or sandwich assays in solutions or on a solid support, precipitation/aggregation assays. In some embodiments, the SAH is assessed by contacting the sample reacted with SAM-dependent homocysteine S-methyltransferase in the presence of SAM with an antibody specific to SAH and with a detectable hapten for the antibody other than the SAH, and wherein determining the presence or amount of the SAH is effected indirectly by determining the presence or amount of the detectable hapten either bound or not bound to the antibody. In some embodiments, the antibody is bound to a carrier matrix.

SAH may also be assessed using a mutant SAH hydrolase having binding affinity for SAH but has attenuated catalytic activity. These mutant SAH hydrolases and assay methods using mutant SAH hydrolases are described in U.S. Pat. No. 6,376,210 and WO 03/060478.

SAH may also be assessed by converting SAH to adenosine and Hcy by SAH hydrolase, and the adenosine generated is assessed. In some embodiments, the SAH is contacted with a SAH hydrolase to generate Hcy from SAM, which is cycled into the Hcy conversion reaction by the SAM-dependent homocysteine S-methyltransferase to form a Hcy co-substrate based enzyme cycling reaction system, and adenosine (Ado), which is assessed to determine the presence, absence and/or amount of the Hcy in the sample.

In some embodiments, the present invention provides a method for assaying homocysteine in a sample, which method comprises: a) methylating homocysteine, if present in a sample, using a methyl donor, e.g., S-adenosylmethionine (SAM) and a SAM-dependent homocysteine S-methyltransferase to form methionine and S-adenosyl-L-homocysteine (SAH); b) releasing adenosine (Ado) from said formed SAH and generating homocysteine using an enzyme S-adenosyl-L-homocysteine hydrolase; and c) assessing said released Ado to determine presence and/or amount of homocysteine in said sample. The method can further include measuring the released amounts of Ado over time. Preferably, steps a) and b) are cycled to release said Ado at rate that can be correlated to the concentration of homocysteine in the sample. Also preferably, the rate of release of the Ado is correlated with standard homocysteine values of concentration. Any suitable methyl donors and methyltransferases can be used. For example, the methyl donor can be SAM and the methylation enzyme can be a SAM-dependent homocysteine methyltransferase. Preferably, the methyl donor SAM is provided in a concentration of at least approximately 5 µM. The rate of Ado formation can be measured using any suitable methods. For example, the rate of Ado formation can be measured enzymatically. Preferably, the rate of Ado formation is measured using Ado deaminase, glutamate dehydrogenase, purine nucleoside phosphorylase, xanthine oxidase, peroxidase, adenosine kinase, or a combination of any two or more of these enzymes. These assay methods are further described herein.

The SAM can be used in any suitable form. For example, the SAM is added to the sample directly. In another example, the SAM is produced by a further reaction, e.g., produced from ATP and Met by a SAM synthase.

Any SAH hydrolase can be used. For example, the nucleic acid molecules containing nucleotide sequences with the GenBank accession Nos. M61831–61832 can be used in obtaining nucleic acid encoding SAH hydrolase (See Coulter-Karis and Hershfield, Ann. Hum. Genet., 53(2): 169–175 (1989)). Also preferably, the nucleic acid molecule containing the sequence of nucleotides or encoding the amino acids described in U.S. Pat. No. 5,854,023 can be used to obtain SAH hydrolase.

Various reducing reagents can be used (for example DTT, TCEP, cysteine, mercaptoethanol, dithioerythritol, sodium borohydride, etc.), however DTT is particularly suitable, e.g., at about 5 mM concentration. DTT should itself be stored at low pH and thus the assay kit can conveniently include a solution of DTT at a low pH (e.g., about 3) but with a low buffer capacity and a separate solution of SAH-hydrolase, which may be partially or totally inactive, at substantially neutral pH and preferably buffered. When these solutions are combined, the enzyme is reactivated at neutral pH. This combination can if desired take place in the presence of the test sample, or with the test sample added shortly thereafter. The other reducing agents mentioned above may similarly be used for both SAH-hydrolase stabilization/activation. TCEP can be stored at a neutral pH, which allows the enzymes to be included in the same reagent with the reducing agent.

The Ado may be assessed by any suitable methods known in the art such as immunological or enzymatic methods. Generally methods relying upon photometric (e.g. calorimetric, spectrophotometric or fluorometric) detection and immunological methods may be used as these may particularly readily be adapted for use in clinical laboratories. Methods based on enzymatic reaction or reaction with mono- or polyclonal antibodies can also be used, as these are simple and quick and can be relatively inexpensive to perform. For example, the Ado may be assessed by monitoring the reaction with enzymes which convert it directly or indirectly to products which may be detected photometrically, e.g., spectrophotometrically. Suitable enzymes, which should of course be non-reactive with the other substrates of the homocysteine converting enzyme, particularly homocysteine, include adenosine deaminase (which converts adenosine to inosine) and adenosine kinase (which converts adenosine and ATP to ADP and phosphorylated adenosine). Such enzymes may further be combined with other enzymes which act to convert the products formed to further detectable products.

Thus exemplary Ado detection schemes useful in the assay of the invention include:

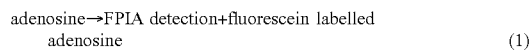

adenosine→FPIA detection+fluorescein labelled adenosine     (1)

adenosine→inosine+NH$_3$     (2)

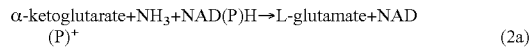

α-ketoglutarate+NH$_3$+NAD(P)H→L-glutamate+NAD(P)$^+$     (2a)

inosine→hypoxanthine     (2b1)

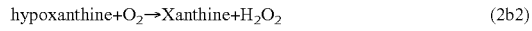

hypoxanthine+O$_2$→Xanthine+H$_2$O$_2$     (2b2)

Xanthine+O$_2$→uric acid+H$_2$O$_2$     (2b3)

2H₂O₂+4−AA (aminoantipyrine)+TOOS (N-ethyl-N-
(2-hydroxy-3-sulfopropyl)-m-toluidine)
→Quinone Dye+4 H₂O                                         (2b4)

Adenosine+ATP→Adenosine-5'-P+ADP                            (3)

Phosphoenolpyruvate+ADP+H³⁰ →pyruvate+ATP                   (3a)

pyruvate+NADH→Lactate+NAD³⁰                                 (3b)

In scheme (1), an immunoassay is conducted and the fluorescein labelled adenosine can be detected.

In scheme (2), the reaction is catalyzed by an adenosine deaminase and the ammonia generated by the adenosine deaminase reaction may readily be detected using known methods, e.g., colorimetric techniques. Thus for example the ammonia generated in the sample may be reacted to form colored products, the formation of which may be detected spectraphotometrically.

In scheme (2a), the reaction is catalyzed by L-glutamate dehydrogenase and the NAD(P)⁺ can be spectraphotometrically detected at 340 nm.

In scheme (2b1), the reaction is catalyzed by a purine nucleoside phosphorylase. In schemes (2b2) and (2b3), the reactions are catalyzed by a xanthine oxidase. In scheme (2b4), the reaction is catalyzed by a peroxidase. The inosine and uric acid have distinctive UV absorption properties and can thus be monitored spectraphotometrically, by kinetic measurements. However the use of UV detection of uric acid or inosine has certain limitations in that the sensitivity of the method is rather poor and it requires a UV-light source and a UV-transparent sample container. It may thus be more convenient to rely upon colorimetric detection of the Quinone dye at 550 nm.

Alternatively, in scheme (2b); the xanthine oxidase reaction lends itself to detection using fluorogens or chromogens, e.g., red-ox indicators, by assessing the reduction/oxidation potential, or by measuring O₂ consumption, or more particularly H₂O₂ formation, for example by the use of electronic sensors. Numerous red-ox indicators can be used for this purpose, and a wide range of methods are described in the literature for assaying H₂O₂ and O₂ in solution. Indeed, H₂O₂ is frequently detected in clinical assays. Hydrogen peroxide, for example, can also be assessed using the non enzymatic chemiluminescent reactions of peroxioxalate and the acridinium esters, the latter in aqueous solution at neutral pH.

In scheme (3), the reaction is catalyzed by an adenosine kinase. In scheme (3a), the reaction is catalyzed by a pyruvate kinase. In scheme (3b), the reaction is catalyzed by a lactate dehydrogenase. The NAD(P)⁺ generated in scheme (3b) can be spectraphotometrically detected at 340 nm.

Any adenosine deaminase can be used for scheme (2). For example, the adenosine deaminase from bovine spleen (Sigma-Aldrich catalog Nos. A5168, 6648 and 5043), from calf intestinal mucosa (Sigma-Aldrich catalog Nos. 01898, A9876 and A1030) or human adenosine deaminase from human erythrocytes (Sigma-Aldrich catalog No. BCR647) can be used. In another example, the adenosine deaminase encoded by the nucleic acids having the GenBank accession No. U76422 (Human, see also Lai, et al., *Mol. Cell. Biol.*, 17(5):2413–24 (1997)) can be used.

Any purine nucleoside phosphorylase can be used for scheme (2b). For example, the purine nucleoside phosphorylase encoded by the nucleic acids having the following GenBank accession Nos. can be used: U88529 (*E.coli*); U24438 (*E.coli*, see also Cornell and Riscoe, *Biochim. Biophys. Acta*, 1396(1):8–14 (1998)); U83703 (*H. pylori*); and M30469 (*E.coli*).

Any xanthine oxidase can be used for scheme (2b). For example, the xanthine oxidase encoded by the nucleic acids having the following GenBank accession Nos. can be used: AF080548 (Sinorhizobium meliloti); and U39487 (Human, see also Saksela and Raivio, *Biochem. J.*, 315(1):235–9 (1996)).

Any adenosine kinase can be used for scheme (3). For example, the adenosine kinase encoded by the nucleic acids having the following GenBank accession Nos. can be used: NM_006721 (*Homo sapiens*); NM_001532 (*Homo sapiens*); NM_001123 (*Homo sapiens*); NM_021129 (*Homo sapiens*); and BC003568 (*Homo sapiens*). The adenosine kinase disclosed in U.S. Pat. No. 5,861,294, McNally et al., *Biochem. Biophys. Res. Commun.* 231:645–650 (1997), and Singh et al., *Eur. J. Biochem.* 241:564–571 (1996) can also be used.

Any glutamate dehydrogenase can be used for scheme (2a). For example, the glutamate dehydrogenase (or glutamic acid dehydrogenase) disclosed in Perez-de la Mora et al., *Anal. Biochem.*, 180(2):248–52 (1989) and Gore, *Int. J. Biochem.*, 13(8):879–86 (1981) can be used.

Any pyruvate kinase can be used for scheme (3a). For example, the pyruvate kinase from porcine (Sigma-Aldrich catalog No. K4388), *Bacillus stearothermophilus* (Sigma-Aldrich catalog No. P1903), chicken muscle (Sigma-Aldrich catalog No. P5788) and rabbit muscle (Sigma-Aldrich catalog No. 83330) can be used.

Any lactate dehydrogenase can be used for scheme (3b). For example, the lactate dehydrogenase from Human (Sigma-Aldrich catalog No. BCR404), *Lactobacillus leichmanii* (Sigma-Aldrich catalog No. 61306), *Lactobacillus* sp (Sigma-Aldrich catalog No. 59023) and rabbit muscle (Sigma-Aldrich catalog No. 61311) can be used.

The methods described herein can be used to assay any sample, e.g., a body fluid or a biological tissue. Exemplary body fluids include urine, blood, plasma, serum, saliva, semen, stool, sputum, cerebral spinal fluid, tears, mucus and amniotic fluid. Preferably, the body fluid to be assayed is blood. The blood sample can be assayed directly or be treated before assaying. For example, the blood sample can be further separated into a plasma or serum fraction.

Prior to or concurrently with the contact between the sample and the Hcy co-substrate and the Hcy converting enzyme, oxidized or conjugated Hcy in the sample can be converted into reduced Hcy. In the plasma or urine, significant proportions of the homocysteine present may be bound by disulphide linkage to circulating proteins, such as albumin, and homocysteine may also be present in the form of other disulphide derivatives (generally homocysteine—cysteine conjugates). To obtain an estimate of total homocysteine present in the sample it may therefore be desirable to treat the sample with a reducing agent to cleave the disulphide bonds and liberate free homocysteine.

Any suitable reducing agent can be used. Disulphides are easily and specifically reduced by thiols (e.g. tri-n-butylphosphine (TBP), dithiothreitol (DTT), dithioerythritol (DTE), 2-mercapto-ethanol, cysteine-thioglycolate, thioglycolic acid, tris(2-carboxyethyl)phosphine, free metals, glutathione and similar compounds). Direct chemical reduction can be achieved using borohydrides (e.g. sodium borohydride) or amalgams (e.g. sodium amalgam) or more specialized reagents such as phosphines or phosphorothioates can be used. Disulphide reduction is reviewed by Jocelyn in Methods of Enzymology 143: 243–256 (1987) where a wide range of suitable reducing agents is listed. The reducing agent can also be tris(2-carboxyethyl)-phosphine hydrochloride (TCEP). Preferably, the dithiothreitol or TCEP is provided in a concentration of up to approximately 30 mM.

The method of the invention may further comprise a step of removing the reducing agent used to convert oxidized or conjugated Hcy into reduced Hcy prior to or concurrently with contacting the sample with the Hcy co-substrate and the Hcy converting enzyme. For example, the reducing agent can be removed by addition of N-ethylmaleimide or other thio-reacting compounds

C. KITS FOR ASSAYING HOMOCYSTEINE

In another aspect, the present invention is directed a kit for assaying Hcy in a sample, which kit comprises: a) a Hcy converting enzyme; b) a Hcy co-substrate; and c) a reagent for assessing Hcy co-substrate conversion product.

In some embodiments, the Hcy co-substrate is S-adenosylmethionine (SAM), the Hcy converting enzyme is a S-adenosylmethionine (SAM)- dependent homocysteine S-methyltransferase, and the Hcy co-substrate conversion product is S-adenosyl-L-homocysteine (SAH). In some embodiments, the reagent for assessing Hcy co-substrate conversion product SAH is an antibody that specifically binds to SAH.

In another aspect, the invention is directed to a kit for assaying Hcy in a sample, which kit comprises: a) a S-adenosylmethionine (SAM)- dependent homocysteine S-methyltransferase; b) S-adenosylmethionine (SAM) or ATP, Met and a SAM synthase; c) a SAH hydrolase; and d) a reagent for assessing adenosine (Ado).

In still another aspect, the invention is directed to a kit for assaying Hcy in a sample, which kit comprises: a) a S-adenosylmethionine (SAM)- dependent homocysteine S-methyltransferase; b) S-adenosylmethionine (SAM) or ATP, Met and a SAM synthase; and c) a reagent for assessing SAH, wherein the kit does not comprise an enzyme or a reagent for generating $H_2O_2$ and a reagent for detecting $H_2O_2$.

In some embodiments, the reagent for assessing Ado comprises an adenosine converting enzyme other than the SAH hydrolase. In some embodiments, the adenosine converting enzyme is an adenosine kinase. In other embodiments, the adenosine converting enzyme is an adenosine deaminase.

The kit described herein can further comprise a reducing agent, e.g., dithiothreitol or tris(2-carboxyethyl)-phosphine hydrochloride (TCEP).

The kits of the invention may be in any suitable packaging. For example, the packages discussed herein in relation to diagnostic systems are those customarily utilized in diagnostic systems. Such packages include glass and plastic, such as polyethylene, polypropylene and polycarbonate, bottles and vials, plastic and plastic-foil laminated envelopes and the like. The packages may also include containers appropriate for use in auto analyzers. The packages typically include instructions for performing the assays described herein.

D. EXAMPLES

The following examples are included for illustrative purposes only and are not intended to limit the scope of the invention.

Example 1

GLDH-NADH Coupling to Detect $NH_4^+$ Generated by the Enzymatic Cycling Using Purified SAM In this study, the following coupled enzymatic cycling reactions are used:

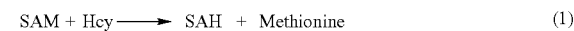

$$SAM + Hcy \longrightarrow SAH + Methionine \quad (1)$$

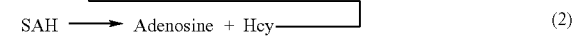

$$SAH \longrightarrow Adenosine + Hcy \quad (2)$$

$$Adenosine \longrightarrow Inosine + NH_4^+ \quad (3)$$

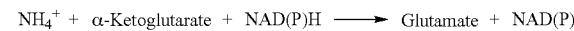

$$NH_4^+ + \alpha\text{-Ketoglutarate} + NAD(P)H \longrightarrow Glutamate + NAD(P) \quad (4)$$

In scheme (1), the reaction is catalyzed by a SAM-dependent homocysteine S-methyltransferase. In scheme (2), the reaction is catalyzed by a SAH hydrolase. In scheme (3), the reaction is catalyzed by an adenosine deaminase. In scheme (4), the reaction is catalyzed by a L-glutamate dehydrogenase. The $NAD(P)^+$ is spectraphotometrically detected at 340 nm. A more deteiled desciprtion of the reagents used in this study is set forth in the following Tables 1 and 2.

TABLE 1

Compositions of Reagent 1

| Chemical Reagent 1 | Concentration |
| --- | --- |
| Potassium phosphate | 15 mM |
| NAD(P)H | 5 mM |
| GLDH | 2 KU/L |
| BSA | 1.2 g/L |
| Adenosine Deaminase | 50 KU/L |
| Homocysteine methyltransferase | 10 KU/L |
| DTT | 0.2 mM |
| α-ketoglutarate | 30 mM |
| SAM | 3 mM |

TABLE 2

Compositions of Reagent 2

| Chemicals Reagent 2 | Concentration |
| --- | --- |
| Tris-HCl | 15 mM |
| BSA | 1.2 g/L |
| SAH hydrolase | 10 KU/L |

In this study, 180 μl of reagent 1 was mixed with 20 μl of a serum or plasma sample to be tested and the mixture was incubated at 37° C. for 5 minutes. Sixty (60) μl of reagent 2 was then added to the mixture and was incubated at 37° C. for another 5 minutes. The change of the absorbance at 340 nm was measured for 2–5 minutes after the reagent 2 was added. One exemplary test result was shown in FIG. 2.

Example 2

GLDH-NADH Coupling to Detect $NH_4^+$ Generated by the Enzymatic Cycling Using SAM Concurrently Converted by SAM Synthase from ATP and Methionine In this study, the following coupled enzymatic cycling reactions are used:

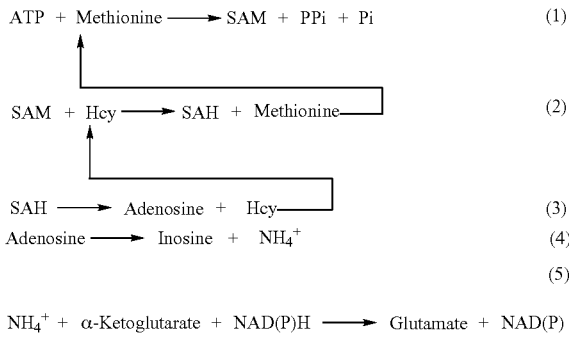

$$Adenosine \longrightarrow Inosine + NH_4^+ \quad (4)$$

$$NH_4^+ + \alpha\text{-Ketoglutarate} + NAD(P)H \longrightarrow Glutamate + NAD(P) \quad (5)$$

In scheme (1), the reaction is catalyzed by a SAM Synthase. In scheme (2), the reaction is catalyzed by a SAM-dependent homocysteine S-methyltransferase. In scheme (3), the reaction is catalyzed by a SAH hydrolase. In scheme (4), the reaction is catalyzed by an adenosine deaminase. In scheme (5), the reaction is catalyzed by a L-glutamate dehydrogenase. The $NAD(P)^+$ is spectraphotometrically detected at 340 nm. A more deteiled descirption of the reagents used in this study is set forth in the following Tables 3 and 4.

TABLE 3

Compositions of Reagent 3

| Chemical Reagent 3 | Concentration |
|---|---|
| Good's buffer | 15 mM |
| NAD(P)H | 5 mM |
| GLDH | 2 KU/L |
| BSA | 1.2 g/L |
| TCEP | 0.2 mM |
| α-ketoglutarate | 30 mM |
| ATP | 10 mM |
| Methionine | 5 mM |
| SAM Synthase | 10 KU/L |
| Adenosine Deaminase | 50 KU/L |
| Homocysteine methyltransferase | 20 KU/L |
| ZnCl2 | 10 mM |

TABLE 4

Compositions of Reagent 4

| Chemicals Reagent 4 | Concentration |
|---|---|
| Sodium phosphate | 15 mM |
| BSA | 1.2 g/L |
| SAH hydrolase | 10 KU/L |

In this study, 270 μl of reagent is mixed with 20 μl of a serum or plasma sample to be tested and the mixture is incubated at 37° C. for 5 minutes. Sixty (90) μl of reagent 2 is then added to the mixture and was incubated at 37° C. for another 5 minutes. The change of absorbance at 340 nm is measured for 2–5 minutes after the reagent 2 is added.

Example 3

Adenosine Kinase—Pyruvate Kinase—Lactate Dehydrogenase—NADH Coupling to Detect Adenosine Generated by the Enzymatic Cycling In this study, the following coupled enzymatic cycling reactions are used:

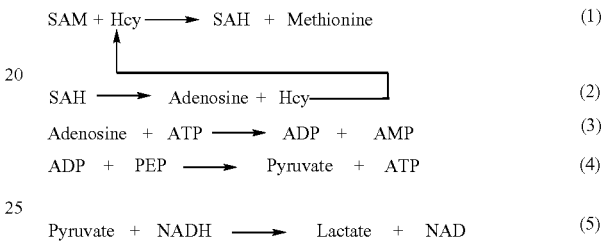

$$Adenosine + ATP \longrightarrow ADP + AMP \quad (3)$$

$$ADP + PEP \longrightarrow Pyruvate + ATP \quad (4)$$

$$Pyruvate + NADH \longrightarrow Lactate + NAD \quad (5)$$

In scheme (1), the reaction is catalyzed by a SAM-dependent homocysteine S-methyltransferase. In scheme (2), the reaction is catalyzed by a SAH hydrolase. In scheme (3), the reaction is catalyzed by an adenosine kinase. In scheme (4), the reaction is catalyzed by a pyruvate kinase. In scheme (5), the reaction is catalyzed by a lactate dehydrogenase. The $NAD(P)^+$ is spectraphotometrically detected at 340 nm. A more deteiled description of the reagents used in this study is set forth in the following Tables 5 and 6.

TABLE 5

Compositions of Reagent 5

| Chemical Reagent 5 | Concentration |
|---|---|
| Potassium phosphate | 15 mM |
| NADH | 5 mM |
| GLDH | 2 KU/L |
| BSA | 1.2 g/L |
| Adenosine Kinase | 10 KU/L |
| Homocysteine methyltransferase | 10 KU/L |
| DTT | 0.2 mM |
| MgCl2 | 15 mM |
| Pyruvate Kinase | 5 KU/L |
| Lactate Dehydrogenase | 25 KU/L |
| SAM | 3 mM |

TABLE 6

Compositions of Reagent 6

| Chemicals Reagent 6 | Concentration |
|---|---|
| Tris-HCl | 15 mM |
| BSA | 1.2 g/L |
| SAH hydrolase | 10 KU/L |

In this study, 180 μl of reagent is mixed with 20 μl of a serum or plasma sample to be tested and the mixture is incubated at 37° C. for 5 minutes. Sixty (60) μl of reagent 2 is then added to the mixture and was incubated at 37° C. for another 5 minutes. The change of absorbance at 340 nm is measured for 2–5 minutes after the reagent 2 is added.

The above examples are included for illustrative purposes only and are not intended to limit the scope of the invention. Many variations to those described above are possible. Since modifications and variations to the examples described above will be apparent to those of skill in this art, it is intended that this invention be limited only by the scope of the appended claims.

The claimed invention is:

1. A method for assaying homocysteine (Hcy) in a sample, which method comprises:
  a) contacting a sample containing or suspected of containing Hcy with a Hcy co-substrate and a Hcy converting enzyme in a Hcy conversion reaction to form a Hcy conversion product and a Hcy co-substrate conversion product, wherein the Hcy co-substrate is S-adenosylmethionine (SAM), the Hcy converting enzyme is a S-adenosylmethionine (SAM)-dependent homocysteine S-methyltransferase, the Hcy conversion product is methionine (Met) and the Hcy co-substrate conversion product is S-adenosyl-L-homocysteine (SAH);
  b) contacting the SAH generated in step (a) with a SAH hydrolase to generate Hcy, which is cycled into the Hcy conversion reaction by the SAM-dependent homocysteine S-methyltransferase to form a Hcy co-substrate based enzyme cycling reaction system, and adenosine (Ado), which is assessed to determine the presence, absence and/or amount of the Hcy in the sample.

2. The method of claim 1, wherein the Ado is assessed by contacting the Ado with an adenosine converting enzyme other than the SAH hydrolase.

3. The method of claim 2, wherein the assessment of the Ado is effected indirectly by assessment of a co-substrate or a reaction product of adenosine conversion by the adenosine converting enzyme.

4. The method of claim 3, wherein the adenosine converting enzyme is an adenosine kinase.

5. The method of claim 3, wherein the adenosine converting enzyme is an adenosine deaminase.

6. The method of claim 1, wherein the sample is a body fluid or a biological tissue.

7. The method of claim 6, wherein the body fluid is selected from the group consisting of urine, blood, plasma, serum, saliva, semen, stool, sputum, cerebral spinal fluid, tears, mucus and amniotic fluid.

8. The method of claim 6, wherein the body fluid is blood.

9. The method of claim 8, wherein the blood is further separated into a plasma or serum fraction.

10. The method of claim 1, wherein prior to or concurrently with the contact between the sample and the ilcy co-substrate and the Hcy converting enzyme, oxidized or conjugated Hcy in the sample is converted into reduced Hcy.

11. The method of claim 1, wherein the Ado is assessed without chromatographic separation.

12. The method of claim 1, wherein the SAM is added to the sample.

13. The method of claim 1, wherein the SAM is produced from ATP and Met by a SAM synthase.

14. A kit for assaying Hcy in a sample, which kit comprises:
  a) a S-adenosylmethionine (SAM)- dependent homocysteine S-methyltransferase;
  b) S-adenosylmethionine (SAM); or ATP, Met and a SAM synthase;
  c) a SAH hydrolase; and
  d) a reagent for assessing adenosine (Ado).

15. The kit of claim 14, wherein the reagent for assessing Ado comprises an adenosine converting enzyme other than the SAH hydrolase.

16. The kit of claim 15, wherein the adenosine converting enzyme is an adenosine kinase or an adenosine deaminase.

17. The method of claim 1, wherein the homocysteine in the sample is assayed without chromatographic separation.

18. The kit of claim 14, which further comprises an instruction for performing a method for assaying homocysteine (Hcy) in a sample, which method comprises:
  a) contacting a sample containing or suspected of containing Hcy with a Hcy co-substrate and a Hcy converting enzyme in a Hcy conversion reaction to form a Hcy conversion product and a Hcy co-substrate conversion product, wherein the Hcy co-substrate is S-adenosylmethionine (SAM), the Hcy converting enzyme is a S-adenosylmethionine (SAM)-dependent homocysteine S-methyltransferase, the Hcy conversion product is methionine (Met) and the Hcy co-substrate conversion product is S-adenosyl-L-homocysteine (SAH);
  b) contacting the SAH generated in step (a) with a SAH hydrolase to generate Hcy, which is cycled into the Hcy conversion reaction by the SAM-dependent homocysteine S-methyltransferase to form a Hcy co-substrate based enzyme cycling reaction system, and adenosine (Ado), which is assessed to determine the presence, absence and/or amount of the Hcy in the sample.

19. The kit of claim 18, wherein at least one of the S-adenosylmethionine (SAM)-dependent homocysteine S-methyltransferase, S-adenosylmethionine (SAM), ATP, Met, the SAM synthase, the SAH hydrolase, and/or the reagent for assessing adenosine (Ado) is packaged in a container.

20. The kit of claim 19, wherein the container is a glass or plastic container.

* * * * *